United States Patent [19]
Vila et al.

[11] Patent Number: 5,571,839
[45] Date of Patent: Nov. 5, 1996

[54] D-ASPARTIC ACID β-HYDROXAMATE FOR THE TREATMENT OF VIRAL INFECTIONS AND TUMORS

[75] Inventors: Jorge Vila, Irigny; Nicole Thomasset, Villeurbanne; Farid Hamedi Sangsari, Lyons; Jacques Grange, Oullins, all of France

[73] Assignee: Institut National de la Sante et de la Recherche Medicale (INSERM), Paris, France

[21] Appl. No.: 34,399

[22] Filed: Mar. 19, 1993

Related U.S. Application Data

[62] Division of Ser. No. 768,324, Oct. 28, 1991, abandoned.

[30] Foreign Application Priority Data

Apr. 28, 1989 [FR] France ................................. 89 05744

[51] Int. Cl.$^6$ ............................. A01N 37/18; A01N 37/30
[52] U.S. Cl. .......................... 514/564; 514/561; 514/563; 562/564; 562/567
[58] Field of Search .................................. 514/561, 563; 562/567, 564

[56] References Cited

FOREIGN PATENT DOCUMENTS 216510    4/1987    European Pat. Off. .
0250335  12/1987    European Pat. Off. .

OTHER PUBLICATIONS

Abstract to EP 250335 23 Dec. 1987 Dore et al.
Gardner, "Amino Acid Analysis in the Study of Protein Digestion and Absorption", Chpt. 10, *Amino Acid Analysis in the Study of Physiological Processes*, Part 2, pp. 158–187, 1985.
Geran et al., *Protocols for Screening Chemical Agents and Natural Products Against Animal Tumors and Other Biological Systems*, 1973 Mar., pp. 1, 47–56, 57.
DeVita et al., "Cancer Drug Development" *Cancer Principles and Practice of Oncology* $2^{nd}$ Ed., pp. 271–274, 1985.
Norton et al., "β–Aspartylhydroxamic Acid: Its Action as a Feedback Inhibitor and a Repressor of Asparagine Synthetase in *Lactobacillus arabinossus*", Archives of Biochemistry and Biophysics 129, pp. 560–566, 1969.
Uren et al., "Effects of Asparagine Synthetase Inhibitors on Asparaginase Resistant Tumors", Biochem. Pharmacology, vol. 26, 15, pp. 1405–1410, 1977.
Translation to EP, A, 0250335, having a publication date of 23 Dec. 1987.
*Cancer Chemotherapy Reports*; Sep. 1972; vol. 3, No. 2; Protocols 4, 11 and 12.

*Primary Examiner*—Gary Geist
*Assistant Examiner*—Dwayne C. Jones
*Attorney, Agent, or Firm*—Oliff & Berridge

[57] ABSTRACT

Beta-hydroxamate D-aspartic acid as a medicine, in particular for treating infectious diseases caused by retroviruses, especially those that cause AIDS, as well as for treating tumors.

13 Claims, 3 Drawing Sheets

D-ASPARTIC ACID β-HYDROXAMATE FOR THE TREATMENT OF VIRAL INFECTIONS AND TUMORS

This is a division of application No. 07/768,324 filed Oct. 28, 1991, abandoned.

The present invention relates to the application as a medicament of D-aspartic acid β-hydroxamate, abbreviated to DAH, of formula:

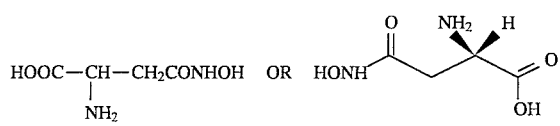

DAH may be formed by the reaction of an activated acyl group of the D isomer of aspartic acid, or one of its derivatives, with hydroxylamine according to the reaction:

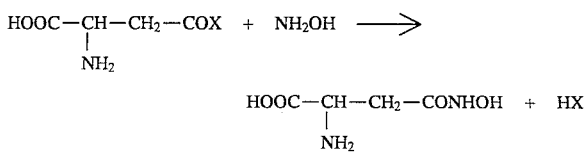

COX being an acid, amide, ester or anhydride group.

DAH may also be prepared enzymatically from D-aspartic acid. It is a known, commercially available product, for example the product A 9009 of the Company SIGMA in the 1987 catalogue (French version).

According to an advantageous and preferred process, DAH is prepared by hydroxyamination of the D-asparagine or of D-aspartic acid β-ethyl ester, the latter being obtained by the monoesterification of D-aspartic acid as shown in the reaction sequence below:

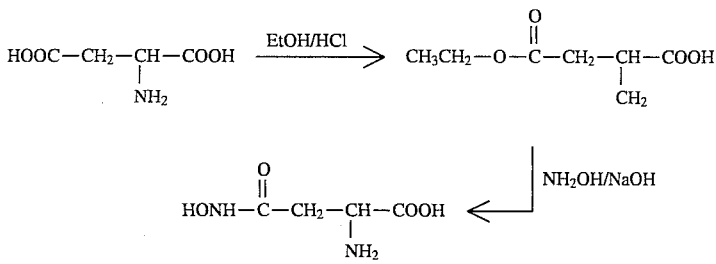

The chemical characterization of DAH is derived, in the first place, from its elemental analysis, which is as follows:
general formula: $C_4H_8N_2O_4$
Molecular weight: 148.1
C=32.56%—H=5.5%—N=18.6%—O=41.98%

DAH is further characterized by the spectral analyses below:

Nuclear magnetic resonance (NMR) analysis:

DAH was analyzed by its $^{13}C$ and $^1H$ NMR spectra, at 50.4 MHz and 200 MHz, respectively, on a Brucker apparatus using Fourier transforms in $D_2O$ solvent. The chemical shifts corresponding to the different signals were expressed in ppm relative to tetramethylsilane (TMS) taken as an external reference.

The $^{13}C$ NMR spectrum contains four characteristic signals corresponding respectively to:
 the acid function (COOH): 172.8 ppm
 the hydroxamate function (CONHOH): 168.4 ppm
 the carbon bearing the $NH_2$ function: 51.1 ppm
 the carbon bearing the $CH_2$ function: 32.2 ppm In the $^1H$ NMR spectrum, the three protons at the α- and β-positions of DAH constitute an ABX type system. Hα is coupled with Hβ (J=7.5 Hz), and each of the two peaks thereby obtained is again split by Hβ' (J=4.5 Hz) and a quadruplet is obtained at 4.2 ppm. Hβ' undergoes splitting of its peak by Hβ (J=16 Hz) and then by Hα (J=4.5 Hz) to give a quadruplet at 3.0 ppm.

In the same manner, Hβ is coupled with Hβ' (J=16 Hz) and with Hα (J=7.5 Hz) to form a quadruplet at 2.9 ppm.

The protons bound to the oxygen and nitrogen atoms are exchanged with D2O and their signals occur at 5 ppm in the peak (HOD).

Mass spectrometry:

The mass spectrum of DAH was established on a VARIAN MAT CHS with an ionization energy of 70 eV. The molecular ion of DAH has zero relative abundance.
m/e (%): $M^+$148 (O); 97 (11); 97 (37); 54 (35); 44 (100); 43 (91); 42 (43); 41 (29); 28 (75); 27 (29); 26 (80); 18 (42); 17 (23).

Spectrophotometry:

The hydroxamate function of DAH is demonstrated by an $Fe^{3+}$-hydroxamate complex which gives a red-violet coloration, quantified by a colorimetric method at 550 nm using a Beckman DU 70 type spectrophotometer.

Stability of DAH:

The stability of DAH as a function of pH and temperature was determined over a period of one month by specific colorimetric assay of the hydroxamate function. The results in the table below show that, in water, DAH is stable up to a temperature of 50° C. A significant degradation of the product is observed only under extreme conditions of pH, as illustrated in Table 1 below.

TABLE 1

Percentage degradation of DAH over a period of 30 days according to pH and temperature.

| Temperature (°C.) | 0.1 N NaOH | $H_2O$ | 0.1 N HCl |
|---|---|---|---|
| +4 | 4% | 0% | 42% |
| +25 | 36% | 0% | 78% |
| +50 | 100% | 0% | 100% |

The subject of the invention is the application of DAH as a medicament, intended especially for the treatment of viral infections, and more especially those due to retroviruses, in particular those causing AIDS, and for the treatment of tumors.

In Patent FR-2,600,256, it was shown that DAH potentiated the antitumor activity of L-asparaginase. It is known, in effect, that L-asparaginase is an antitumor agent. Since this activity proves insufficient, efforts have been made to strengthen it by combining L-asparaginase with other products. Combinations with DAH has not yielded results which can be exploited in practice.

It has now been found, surprisingly, that DAH alone has an antiretroviral activity, especially against the viruses responsible for AIDS. It has also been found that DAH administered at specific doses possesses an inhibitory action on tumors.

It is well known that, despite the progress made in relation to combating viral infections, a range of antiviral agents as extensive, safe and effective as the range of antibiotics, for example, is not yet available.

On the basis of their mode of action, antiviral agents may be classified broadly in three categories, the boundaries between them often being arbitrary: chemical agents, immune system stimulators and activators of the antiviral cell state.

Chemical agents are the most widespread, but their spectrum of action is generally very limited, and they often ultimately select resistant viral variants, in the same manner as do antibiotics with bacteria (DE CLERCQ E., Biochem. J., 206, 1–13, 1982 ; BECKER Y. and HADAR J., Prog. Med. Virol., 26, 1–44, 1980).

Apart from the various types of vaccines, immune response activators are agents capable of activating the body's non-specific defenses (macrophages, natural "killer" cells) or, more rarely, specific defenses ("B" or "T" lymphocytes). For the most part, these agents are still at an experimental stage. In contrast to chemical agents, the essential features of their mode of action are their very broad spectrum of action and the fact that they cannot select resistant variants. However, they are at present limited in number and relatively ineffective, although progress in this direction has recently been made (KOFF W. C., SHOWALTER S. D., HAMPAR B. and FIDLER I. J., Science, 228, 495–496, 1985).

Inducers of the antiviral cell state comprise interferon (IFN), IFN inducers and IFN substitutes. They comprise a still very limited group of substances with the characteristic feature of arousing in cells a state of resistance to viral infection. These agents possess simultaneously a capacity for the action at cell level of chemical agents and the very broad spectrum of action of immune system activators. Since they act on all cells, both infected and otherwise, a decisive factor in their efficacy is their low power of toxicity towards cells.

Among viruses, retroviruses represent a group responsible for conditions which are especially serious and difficult to combat.

Retroviruses and their carcinogenic power are not a new scientific finding. As early as the beginning of the century, several investigators had identified in animals transmissible agents capable of causing leukemia and solid tumors (ROUS P., J. Am. Med. Assoc., 54, 198, 1911). In the course of the following decades, retroviruses were found in many animal species. The sustained efforts of investigators led (lacuna) to the isolation in 1980 of the first human retrovirus: the type I human T lymphocyte lymphotropic virus (HTLV-I) (POIESZ B. J. et al., Proc. Natl Acad. Sci. USA, 77, 7415, 1980). HTLV-1 gives rise to a rare and extremely malignant cancer, T lymphocyte leukemia of adults, which is endemic in certain regions of Japan, of Africa and of the Caribbean.

Another very serious and important condition caused by retroviruses is AIDS.

The first cases of AIDS were diagnosed in 1981 (GOTTREB, M. S. et al., Weekly Record, 30, 250, 1981). The agent responsible, namely the human immunodeficiency virus (HIV), a retrovirus, was discovered in 1983 (BARRE SINOUSSI F. et al., Science, 220, 868, 1983). Agents which are active against this retrovirus are hence currently being sought. In view of the problems involved in the development of a vaccine in the near future, the search for a product capable of inhibiting the replication of this retrovirus is necessary.

Experimental studies relating to antiviral activities frequently involve the disease induced by the Friend virus.

The FLV virus is a type C murine retrovirus which produces rapid effects on erythropoiesis, the erythroid precursors being the target cells of this virus. The Friend complex comprises a transforming virus defective for replication, known as SFFV (spleen focus forming virus) since it is capable of inducing macroscopic foci of transformed cells in the spleen of infected adult mice, and a helper virus, known as F-MuLV (Friend murine leukemia virus), which serves for replication. Two variants of this virus exist: FV-A which induces an anemia and FV-P which produces a polycythemia. The erythroleukemia induced by FL-V exhibits two phases: an early stage characterized by rapid growth in the number of relatively mature erythropoietic precursors with a limited capacity for proliferation, and a late stage characterized by the emergence of undifferentiated precursors with an intense capacity for proliferation. In vivo, the manifestations of this disease are splenomegaly accompanied by hepatomegaly, by erythroid hyperplasia in the spleen and bone marrow, by polycythemia and by macroscopic foci in the spleen. The final phases are characterized by the presence of immortal erythroid cells which can be transplanted.

According to the invention, it has been shown that DAH produces a substantial inhibition of the multiplication of viruses belonging to the retrovirus family, or of viruses whose replication is related thereto, such as the Viruses referred to as "Hepadnaviridae". This has been demonstrated in vitro with the AIDS virus (HIV) and in vivo with the FRIEND virus (FLV—Friend leukemia virus) which is a type C murine retrovirus.

Retroviruses, like any other virus, cannot reproduce without diverting to their own advantage the bio-synthetic apparatus of the cell. The special feature lies in their capacity for reversing the normal flow of genetic information. In retroviruses, the genetic material consists of RNA, which an enzyme, reverse transcriptase, utilizes for synthesizing DNA; this viral DNA can integrate in the genome of the host cell.

The subject of the present invention is also a new medicinal composition intended, in particular, for the treatment of viral infections, especially those linked to AIDS, as well as for the treatment of tumors, characterized in that it contains D-aspartic acid β-monohydroxamate (DAH) as active principle, in a pharmaceutically acceptable vehicle. The composition of the invention can also contain inert or pharmacodynamically active additives.

The medicinal composition of the invention can take the form of a lyophilized powder of the active substance, to be dissolved immediately before use in a physiological solution for the purpose of injection. The medicament can then be administered parenterally, for example intravenously, intraperitoneally, in the cerebrospinal fluid, and the like. For injection, the active principle is dissolved in a physiological solution until the desired concentration for administration is obtained.

The medicinal composition according to the invention can also take a form which is suitable for oral administration. For example, suitable forms are tablets, hard gelatin capsules, dragées, powders and granules.

As regards the dosage of the medicament according to the invention, it will be shown that the doses to be administered are variable according to the treatment period, the frequency of administration, the host and the nature and severity of the disease. The administration of a quantity greater than 1 g and which can range up to several grams of active substance at intervals over a limited period may, for example, be mentioned, as will become apparent from the detailed description below.

The invention also covers the use of D-aspartic acid β-monohydroxamate (DAH) for manufacturing a medicinal composition intended for the treatment of viral infections and tumors.

Another subject of the invention is a process for preparing D-aspartic acid β-monohydroxamate (DAH), comprising the monoesterification of D-aspartic acid for the purpose of obtaining D-aspartic acid β-ethyl ester and hydroxylation of the latter, leading to DAH. DAH may also be prepared by hydroxyamination of D-asparagine.

Finally, the invention covers a process for preparing a pharmaceutical composition, characterized in that D-aspartic acid β-monohydroxamate (DAH) is prepared in the form of a lyophilized powder which is intended for dissolution immediately before use in a physiological solution for the purpose of injection, or alternatively the active substance is put into a form suitable for oral administration, where appropriate with one or more inert or pharmacodynamically active additives.

EFFECT OF DAH ON THE REPLICATION OF HIV

Figure 1:
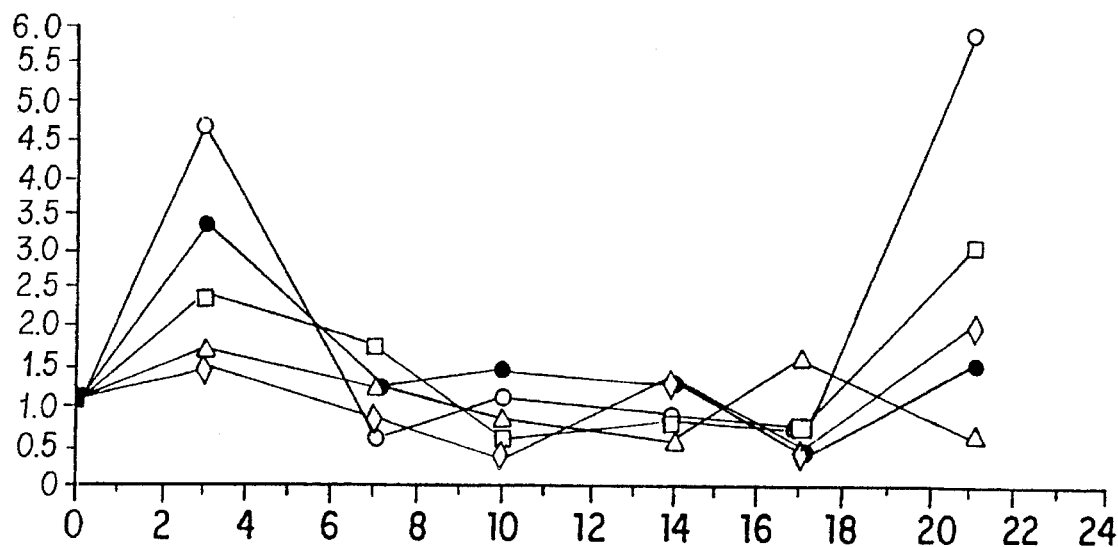
FIG. 1 demonstrates the effect of DAH on the rate of growth of lymphocytes of healthy donors.
Figure 2:
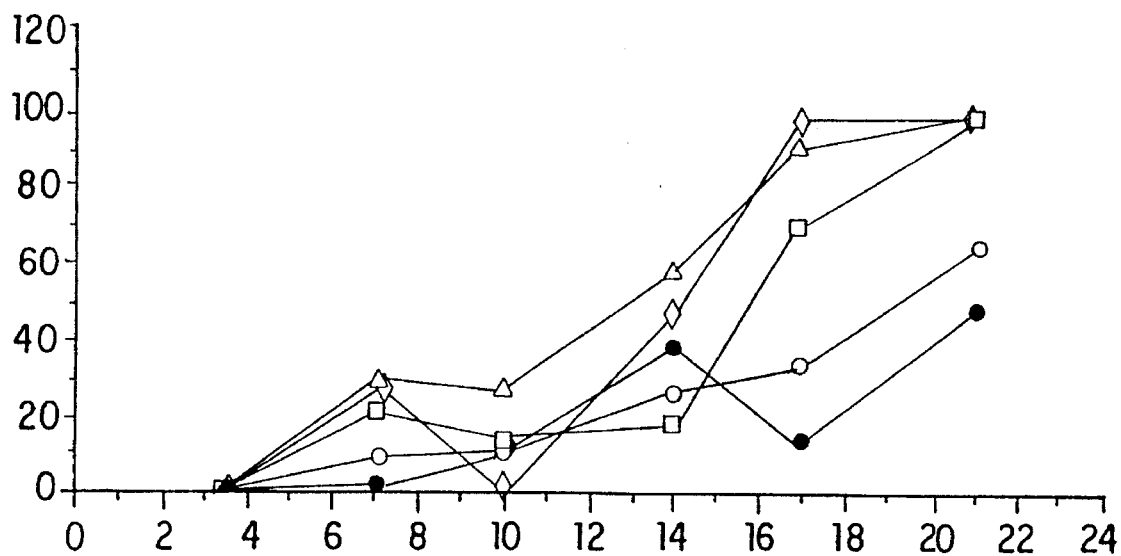
FIG. 2 shows the effect of DAH on the cell mortality of healthy lymphocytes.
Figure 3:
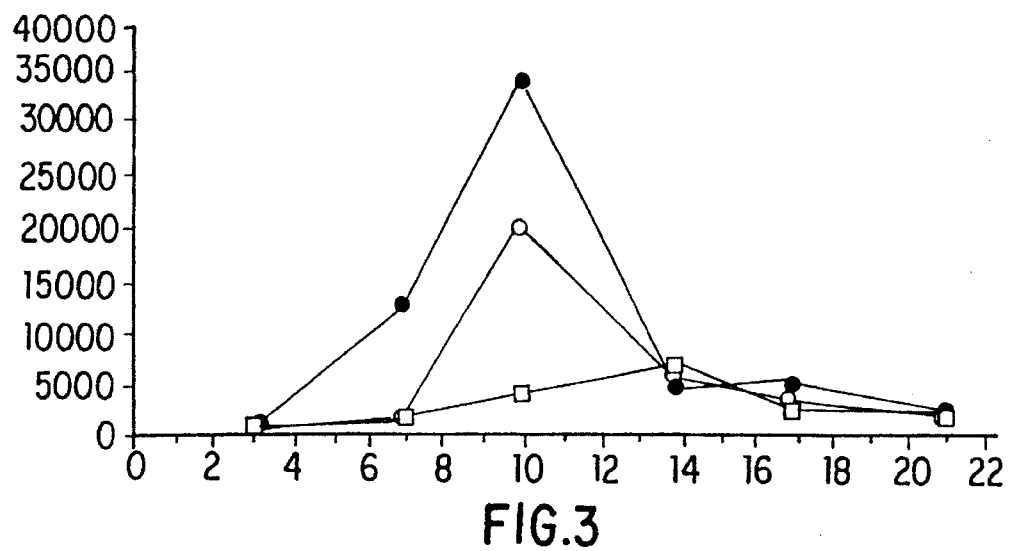
FIG. 3 illustrates the effect of DAH treatment for three days on the production of vital reverse transcriptase by a coculture of lymphocytes of AIDS patients and normal lymphocytes.
Figure 4:
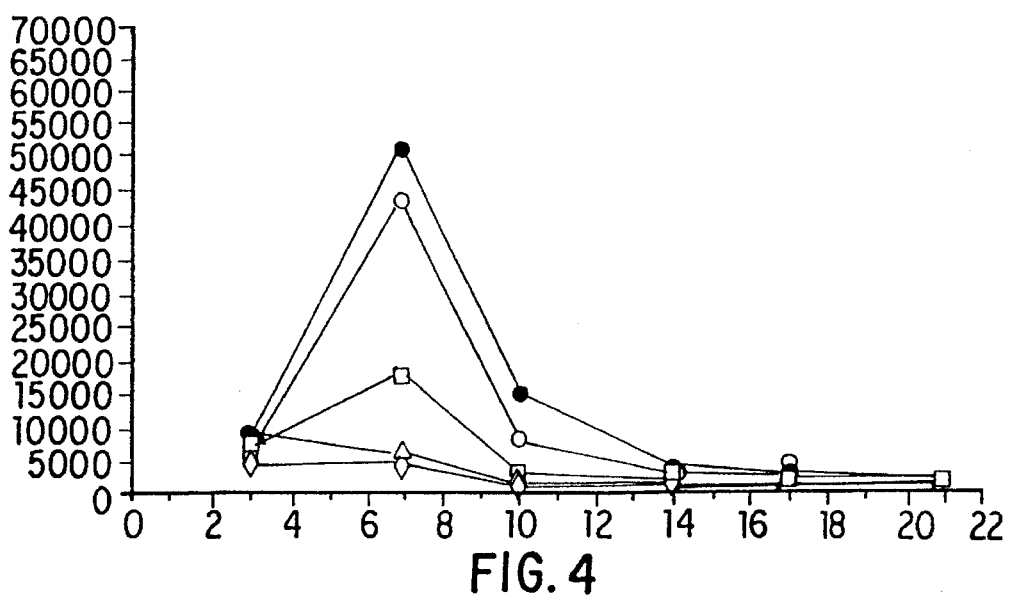
FIG. 4 shows the effect of DAH treatment for three days on the production of viral reverse transcriptase by a culture of lymphocytes infected with the purified virus.
Figure 5:
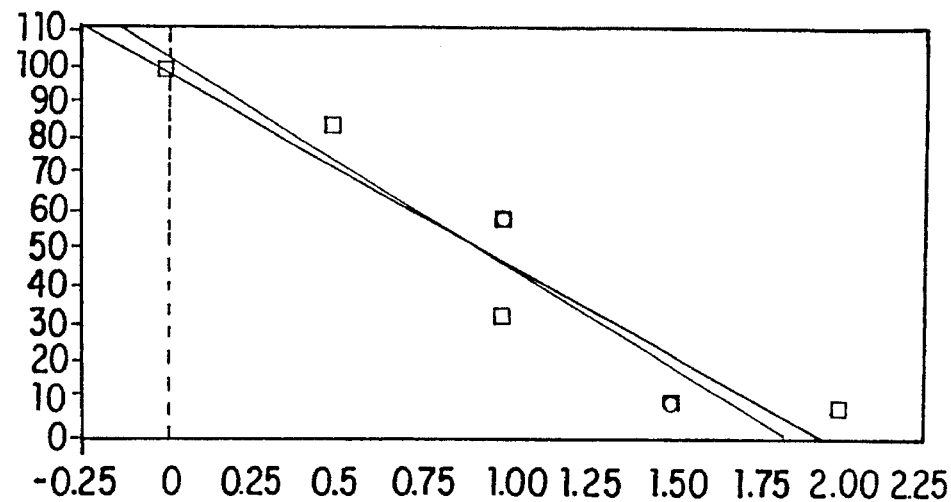
FIG. 5 illustrates the dose effect on the maximum of the peak reverse transcriptase activity.

According to the invention, it has been shown that DAH totally inhibits the viral multiplication of HIV. This inhibition is dose-dependent. The tests first involved lymphocytes of healthy donors (FIGS. 1 and 2). This activity could be demonstrated on two models of replication of HIV: a) normal lymphocytes infected with the purified virus, and b) coculture of lymphocytes of AIDS patients and normal lymphocytes. The reverse transcriptase activity was measured during 22 days in the cell culture supernatant as a criterion of vital proliferation. The treatment with DAH lasted 72 hours from $D_0$ to $D_3$ of the manipulation (FIGS. 3, 4 and 5).

Figure 6:
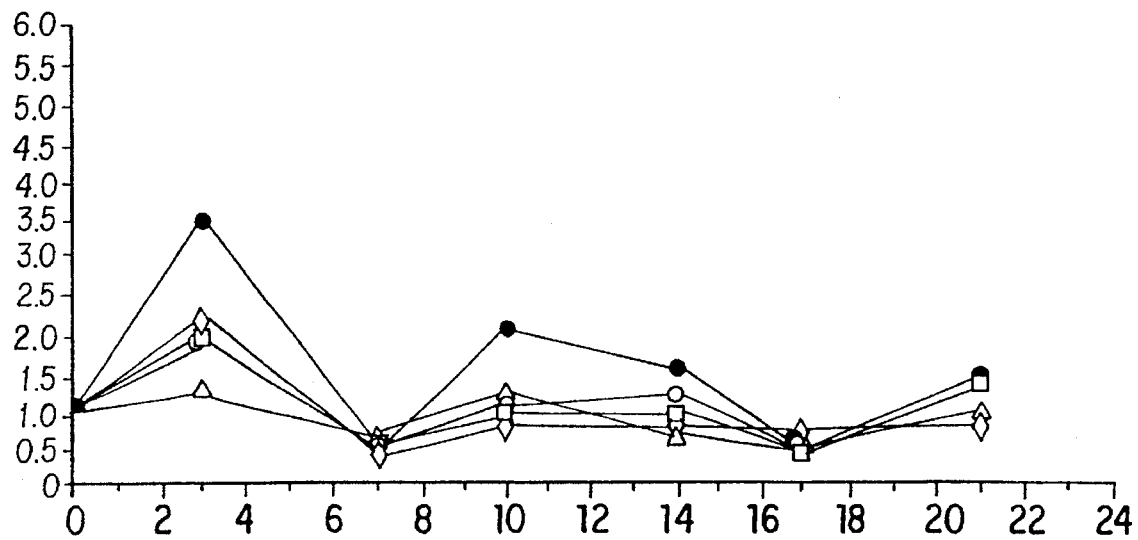
FIG. 6 demonstrates the effect of DAH on the rate of growth of infected lymphocytes.
Figure 7:
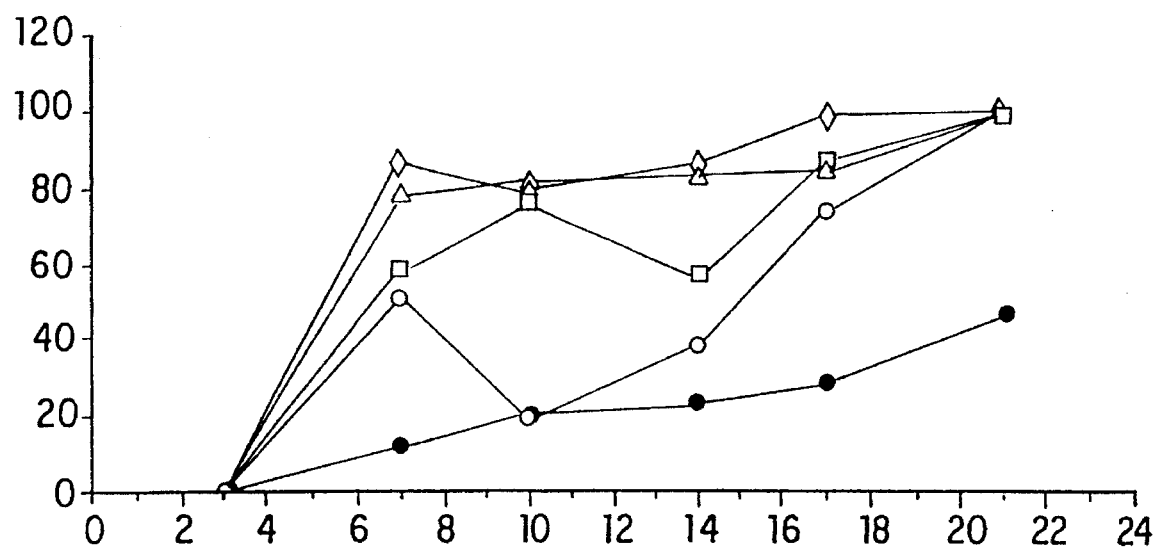
FIG. 7 shows the effect of DAH on cell mortality of infected lymphocytes.

It was found that the lymphocytes proliferated during the treatment with the product, and that this product is not toxic to lymphocytes not infected with the HIV virus (FIGS. 1 and 2). In contrast, DAH was shown to be more toxic with respect to lymphocytes infected with the AIDS virus (FIGS. 6 and 7).

Legend to FIG. 1

Effect of DAH on the rate of growth of lymphocytes of healthy donors.

(●) absence of DAH (o) DAH concentration=0.5 mM (□) DAH concentration=1 mM (Δ) DAH concentration=1.5 mM (◊) DAH concentration=2 mM Abscissae: culture time (in days)

Ordinates: rate of growth

Legend to FIG. 2

Effect of DAH on the cell mortality of healthy lymphocytes.

(●) absence of DAH (o) DAH concentration=0.5 mM (□) DAH concentration=1 mM (Δ) DAH concentration=1.5 mM (◊) DAH concentration=2 mM Abscissae: culture time (in days)

Ordinates: proportion of dead cells (in %)

Legend to FIG. 3

Effect of DAH treatment for three days on the production of viral reverse transcriptase by a coculture of lymphocytes of AIDS patients and normal lymphocytes.

(●) absence of DAH (control)

(o) DAH concentration=1 mM (□) DAH concentration=1.5 mM

Abscissae: time of growth of the cultures after inoculation of DAH (in days)

Ordinates: reverse transcriptase activity CPM/million cells)

Legend to FIG. 4

Effect of DAH treatment for three days on the production of the viral reverse transcriptase by a culture of lymphocytes infected with purified virus.

(●) absence of DAH (control)

(o) DAH concentration=0.5 mM (□) DAH concentration=1.0 mM (Δ) DAH concentration=1.5 mM (◊) DAH concentration=2.0 mM Abscissae: time of growth of the cultures after inoculation of DAH (in days)

Ordinates: reverse transcriptase activity (in CPM/million cells)

Legend to FIG. 5

Dose effect on the maximum of the peak reverse transcriptase activity.

(o) coculture (□) culture infected with purified virus

Abscissae: doses used (in mM)

Ordinates: reverse transcriptase activity.

Legend to FIG. 6

Effect of DAH on the rate of growth of infected lymphocytes.

(●) absence of DAH
(o) DAH concentration=0.5 mM
(□) DAH concentration=1 mM
(Δ) DAH concentration=1.5 mM
(◇) DAH concentration=2 mM
Abscissae: culture time (in days)
Ordinates: rate of growth.
Legend to FIG. 7
Effect of DAH on cell mortality of infected lymphocytes.
(●) absence of DAH
(o) DAH concentration=0.5 mM
(□) DAH concentration=1 mM
(Δ) DAH concentration=1.5 mM
(◇) DAH concentration=2 mM
Abscissae: culture time (in days)
Ordinates: proportion of dead cells (in %).

EFFECT OF DAH ON THE DISEASE INDUCED BY THE FRIEND VIRUS.

The FLV virus is a type C murine retrovirus which produces rapid effects on erythropoiesis, the erythroid precursors being the target cells of this virus. The Friend complex comprises a transforming virus defective for replication, known as SFFV (spleen focus forming virus) since it is capable of inducing macroscopic foci of transformed cells in the spleen of infected adult mice, and of a helper virus, known as F-MuLV (Friend murine leukemia virus), which serves for replication. Two variants of this virus exist: FV-A which induces an anemia and FV-P on which studies have been performed and which produces a polycythemia. The erythroleukemia induced by FL-V exhibits two phases: an early stage characterized by rapid growth in the number of relatively mature erythropoietic precursors with a limited capacity for proliferation, and a late stage characterized by the emergence of undifferentiated precursors with an intense capacity for proliferation. In vivo, the manifestations of this disease are splenomegaly accompanied by hepatomegaly, by erythroid hyperplasia in the spleen and bone marrow, by polycythemia and by macroscopic foci in the spleen. The final phases are characterized by the presence of immortal erythroid cells which can be transplanted.

The effect of DAH on the replication of the Friend virus in cell culture was studied.

Cultures of SC1 cells treated with polybrene were infected with FLV ($5 \times 10^5$ infective particles per $2 \times 10^5$ cells). The cells were then cultured with various concentrations of DAH, and the activity of FLV replication was measured by assaying the reverse transcriptase activity appearing in the culture media supernatants on days 2, 4 and 6 after infection.

A significant inhibition of FLV replication by DAH is observed. The reverse transcriptase activity is lowered by approximately 70% by DAH at a concentration of 0.2 mM, by 80% at a concentration of 0.5 mM and by 90% at a concentration of 1 mM.

On the other hand, it is observed that doses of 0.2 and 0.5 mM DAH have no cytostatic effect on SC1 cells, and that a concentration of 1 mM DAH only moderately inhibits cell division. Thus, the observed anti-FLV effect does not result indirectly from a toxic effect of DAH on cell metabolism, but from a direct effect on the replication of the retrovirus.

Since the reverse transcriptase is the target of various antiretroviral agents, it is advantageous to test the effect of DAH on the reverse transcriptase (RT) activity of FLV. This test was performed using a preparation of highly purified FLV as a source of RT, and poly(A)-oligo(dT) as substrate. The substrates were introduced into the reaction medium in the following order: DAH at the desired concentrations, purified virus, poly(A)-oligo(dT), dTTP+[$^3$H]-dTTP.

The results show that DAH has no effect on the RT activity at concentrations at which the antiretroviral effect is observed in cell culture. DAH in the unmetabolized, native form is hence not an RT inhibitor.

In other tests, the virus was maintained by successive intraperitoneal passages in DBA/2 mice. This maintenance was carried out from the animal's spleen every 21 days. The activity of DAH was assessed by comparing the survival times of animals injected with the virus, with or without DAH. The treatment began three days after viral infection, since this lapse of time is considered to be necessary for there to be sequences of the virus in the genome of the erythroid precursors of the infected mouse. After varying the number of daily injections and the treatment period for a given dose, it was established that 3 injections of 1 g/kg/dose of DAH during the first 10 days and 2 injections of 1 g/kg/dose of DAH during the following 20 days produce a T/C of 239%. The results are recorded in the following table:

TABLE 2

| Active substance | Dose (g/kg) of body weight | Days of treatment | T/C × 100 (%) (2) | Number of surviving animals |
|---|---|---|---|---|
| DAH | 1 × 3/d (1) 1 × 2/d | D 1–30 | 239.86 | 5/10 |
| DAH | 1 × 3/d | D 1–10 | 193 | 0/10 |

(1) The animals are treated 3 times per day from D 1–10 and twice a day from D 11–30.
(2) T/C = ratio of the survival time of the treated animals (T) to the survival time of the control animals (C).

It may be noted that a criterion of activity T/C equal to or greater than 125% is significant.

ANTITUMOR ACTIVITY OF DAH

According to the invention, it has also been shown that DAH, when administered in specific dosages, as are defined below, has an inhibitory action on tumors.

In French Patent FR-2,600,256, cited above, it is reported that DAH showed no activity in vivo, after a treatment with DAH on the basis of 600mg/kg per day for 5 days, in three murine tumor models, namely 1210 leukemia, RBL5 lymphoma and B16 melanoma, the mice having been inoculated with the abovementioned tumor cells. It has now been observed, on the one hand that, in the same types of tests conducted in vitro, inhibition of the growth of the tumor cells (50% IC) takes place with doses of DAH beginning at between 0.8 and 1 mM per liter of cell medium, and on the other hand that, in the murine tumor model of 1210 leukemia, which is renowned for being difficult to cure, an administration of 1 g/kg of body weight at the rate of 4 times a day for 3 days already leads to a very significant prolongation of the survival of the treated animals.

Under these same dosage conditions, L-aspartic acid β-hydroxamate is very toxic. Thus, increasing the doses of the abovementioned D derivative relative to the L derivative reveals an activity of the D derivative without exhibiting the toxicity exhibited by the L derivative at the same dosages (the 50% LD for DAH is 10 g/kg, whereas the 50% LD for LAH is 2.5 g/kg).

The doses employed for the treatment of the mice varied from 0.5 g/kg to 1.5 g/kg for a minimum period of 3 days which can extend up to 10 days.

It proves, however, to be possible to employ higher doses, up to 5 g/kg, and to be the case that, if the dose is low, a longer period of treatment is needed.

In vivo comparative study of DAH and LAH

The antitumor activity of DAH and of LAH was studied on the L1210 leukemia model. L1210 leukemic cells are maintained by intraperitoneal passages in male B6D2F1/J mice. The number of cells used for the therapeutic tests is $10^5$ cells per mouse in 0.5 ml of PBS. The observation period is 30 days.

The results are recorded in the following Table 3:

TABLE 3

| Active substance | Dose (g/kg of body weight) | Days of treatment | T/C × 100 (%) (2) | Number (3) of surviving animals | Weight change (4) |
|---|---|---|---|---|---|
| DAH | 1 × 3/d | 1–10 | 347 | 3/5 | +1.300 |
| DAH | 1.5 × 4/d (1) | 1,2,3,4 | 347 | 3/5 | +1.000 |
| DAH | 1.5 × 4/d | 1,2,3 | 276 | 0/5 | +1.200 |
| DAH | 1 × 4/d | 1,2,3 | 171 | 0/5 | +1.100 |
| DAH | 0.5 × 4/d | 1,2,3 | 113 | 0/5 | +1.400 |
| LAH | 1.5 × 4/d | 1 | 50 | 0/5 | — |
| LAH | 1 × 4/d | 1,2 | 65 | 0/5 | — |

(1) The animals are treated 4 times a day.
(2) T/C = ratio of the survival time of the treated animals (T) to the survival time of the control animals (C).
(3) At 30 days.
(4) Weight change (in grams) from D1–D5.

It is found that DAH manifests a significant antitumor activity in this model with an administration at a dose greater than or equal to 1 g/kg, 3 or 4 times a day. In contrast, for LAH, the same protocol is not applicable on account of the toxicity, and even using a lighter protocol, antitumor activity was not observed, but always a very substantial toxicity (death of the animals treated with LAH before the control group).

The antitumor activity of DAH was also studied on two other murine models: L5178Y lymphoma and P388 leukemia.

Murine lymphoma cells (L5178Y) are maintained by successive intraperitoneal passages in DBA/2 mice, and injected for the tests at a dose of $10^4$ cells per mouse.

P388 leukemia cells are maintained by intraperitoneal passage in DBA/2 mice, and injected for the tests at a dose of 105 (sic) cells per mouse into B6D2F1 mice.

The results are recorded in the following table:

| L5178Y lymphoma | | | | |
|---|---|---|---|---|
| Active substance | Dose (g/kg) of body weight | Days of treatment | T/C × 100 (%) | Number of surviving animals* |
| DAH | 1 × 4/d | 1,2,3,4,5 | 576 | 5/5 |
| DAH | 1 × 3/d | 1,2,3,4,5 | 576 | 5/5 |

*at 120 days.

| P388 leukemia | | | | |
|---|---|---|---|---|
| Active substance | Dose (g/kg) of body weight | Days of treatment | T/C × 100 (%) | Number of surviving animals* |
| DAH | 1.5 × 4/d | 1,2,3,4,5 | 190 | 0/5 |
| DAH | 1.5 × 4/d | 1,2,3 | 155 | 0/5 |

*at 30 days.

In the description which follows, more complete information is given regarding the use of DAH as a medicament.

Preclinical pharmacology

DAH was assayed in the sera and urine of 8-week-old B6D2F1 mice which had received an intraperitoneal injection of DAH of 3 g/kg. The DAH was assayed by spectrophotometry, by detecting the $Fe^{3+}$-hydroxamate complex at 550 nm.

After intraperitoneal injection of DAH, a mean plasma peak of 6 mg/ml was observed at 20 minutes. The decrease in this concentration took place with a halftime of 35 minutes. The urinary peak was observed at 250 minutes after injection with a value of 220 mg/ml. Urinary elimination is sustained over 24 hours. The DAH eliminated in the urine has not undergone any structural modification. DAH hence acts in its native form, without undergoing metabolism.

Toxicological study

Toxicity in mice:

The toxicity of parenterally administered DAH was assessed in six-week-old B6D2F1 mice weighing between 20 and 22 g. For each dose level, thirteen males and thirteen females were used, with an observation period of 14 days. The lethal dose (LD) was assessed 24 hours after the injection of DAH, and then at 14 days. Under these conditions, it could be shown that the $LD_{10}$ (10% mortality) was observed with dosages of 8.5–9 g/kg; the $LD_{50}$ corresponded to 11–12 g/kg and the $LD_{90}$ to 14g–15 g/kg. No significant difference in mortality was observed at 24 hours and at 14 days for a given dose level.

Tolerance to a sustained administration of DAH was assessed on a group of 10 mice treated for 30 days with a daily injection of 2 g/kg, and a group of 10 mice receiving two injections of 1 g/kg per day during the same period. The tolerance was excellent, without a clinical sign of toxicity, without mortality and with a body weight remaining in a range of +/− 10% relative to a control group of the same age and same initial weight.

Toxicity in dogs:

Following the recommendations of the National Cancer Institute (NCI), the following were determined: a) the maximal non-toxic dose, b) the low toxic dose, c) the maximal non-lethal toxic dose, d) the lethal dose.

These studies were carried out on six- to seven-month-old beagle dogs weighing 6.5 to 7.5 kg. To demonstrate the toxic effects of DAH, clinical, morphological, biochemical and hematological parameters were measured.

The assessment of heart rate, electrocardiogram, arterial blood pressure (measured by intra-arterial catheterization) and respiratory rate were measured in dogs anesthetized with alpha-chloralose. In animals which had received an intravenous administration of DAH varying between 1 and 5 g/kg, no modification of these parameters was observed.

Immediate onset toxic effects: the intravenous injection of DAH at doses varying from 1 to 10 g/kg (in 10% solution) caused vomiting during the period of administration of the product. This vomiting disappeared as soon as the perfusion was ended and is accompanied by an anorexia which can be sustained for up to 24 hours, depending on the size of dose administered. No other symptom of intolerance was observed during administration of DAH.

Early onset toxic effects: hematological toxicity. A toxicity towards the platelet line was noted at and above a dose of 5 g/kg, with a nadir of $39 \times 10^9$ platelets/l on day 8 after injection of DAH, and a return to the pretreatment level seven to ten days later. At a dose of 9 g/kg, the thrombocytopenia was more profound, with a nadir at 17×109 (sic) platelets/l 22 days after injection and a partial recovery ($56 \times 10^9$/l) two months later. No toxicity toward granulo/ monocyte or erythrocyte lines was noted, even at high doses (9 g/kg).

No toxicity towards renal or hepatic function was noted at the doses described above. One dog which received a dose of more than 10 g/kg exhibited a precipitation of DAH crystals in the renal tubules, a complication which it has subsequently been possible to avoid by a prehydration with physiological solution.

Repeated intraveneous administration of DAH over two weeks, with five weekly injections of 1 g/kg did not give rise to any sign of intolerance other than vomiting during the period of administration of the product. Biological examinations showed no metabolic or hematological disturbance or disturbance of hemostasis.

These results collectively enable it to be concluded that the maximal non-toxic dose lies between 2.5 and 3 g/kg, that the low toxic dose is 5 g/kg and that the maximal non-lethal toxic dose is of the order of 9 g/kg. This demonstrates the low toxicity of DAH.

DAH may be administered intravenously in continuous fashion to patients suffering from AIDS. To this end, DAH powder is dissolved in a physiological solution, for example at a concentration in the region of 10%. Each vial contains 10 g of DAH for a single dose. The DAH is then administered over 24 h in continuous perfusion via the peripheral venous route.

The preclinical studies presented above provide a value for the $LD_{10}$ of 8.5 g/kg. Taking into account the mouse/man correction factor, the initial dose in humans would hence be 1.2 $g/m^2$ of body surface.

In the light of the activity studies performed in animals, an administration in continuous venous perfusion may be peformed over a period of 15 days, after the patients have received a single dose equal to ¹/₂₄th of the daily dose, in a one-hour perfusion, on the day before treatment by continuous perfusion. This protocol is similar to that which has been employed in the case of azidothymidine (Yarchoan et al., Lancet, 1986, 575–580). An increase in the doses may be applied in the context of medical supervision.

The foregoing description illustrates the practical value of DAH in the treatment of AIDS. Moreover, the use of DAH has been illustrated in the description specifically against the HIV virus, but this use relates to the treatment of all conditions linked to AIDS.

We claim:

1. A method of treating a patient, comprising administering to said patient an independently therapeutically effective amount of DAH, wherein said patient has HIV or FLV viral infection and said DAH is administered in an amount independently effective to inhibit viral replication associated with said viral infection without administering L-asparaginase to said patient.

2. The method according to claim 1, wherein said viral infection is HIV infection.

3. The method according to claim 1, wherein said administering comprises orally administering.

4. The method according to claim 1, wherein said administering comprises parenterally administering.

5. The method according to claim 4, further comprising dissolving a lyophilized powder of said DAH in a physiologic solution prior to administering the DAH.

6. A method of treating a patient, comprising administering DAH to said patient in an amount of at least about 10 g/day without administering L-asparaginase to said patient, wherein said patient has HIV or FLV viral infection.

7. The method according to claim 6, wherein said viral infection is HIV infection.

8. A method of treating a patient, comprising orally administering DAH to said patient, wherein said patient has HIV or FLV viral infection and said DAH is administered in an amount effective to inhibit viral replication associated with said viral infection without administering L-asparaginase to said patient.

9. The method according to claim 8, wherein said viral infection is HIV infection.

10. The method according to claim 8, wherein said DAH is administered in an amount of at least 10 g/day.

11. A method of treating a patient comprising administering to said patient a composition consisting essentially of a therapeutically effective amount of DAH and a carrier, wherein said patient has HIV or FLV viral infection and said DAH is administered in an amount independently effective to inhibit viral replication associated with said viral infection.

12. The method according to claim 11, wherein said viral infection is HIV infection.

13. A pharmaceutical composition comprising an effective amount of DAH and at least one pharmacodynamically active ingredient but not L-asparaginase.

* * * * *